United States Patent
Kowalsky et al.

(10) Patent No.: US 6,964,683 B2
(45) Date of Patent: Nov. 15, 2005

(54) SYSTEM AND METHOD TO EFFECT THE MITRAL VALVE ANNULUS OF A HEART

(75) Inventors: Leonard Kowalsky, Bothell, WA (US); Gregory D. Nieminen, Bothell, WA (US); Ryan H. Braxtan, Snoqualmie, WA (US); Mark L. Mathis, Fremont, CA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 0 days.

(21) Appl. No.: 10/798,728

(22) Filed: Mar. 10, 2004

(65) Prior Publication Data

US 2004/0243228 A1 Dec. 2, 2004

Related U.S. Application Data

(62) Division of application No. 10/331,143, filed on Dec. 26, 2002, now Pat. No. 6,793,673.

(51) Int. Cl.⁷ ................................................. A61F 2/24
(52) U.S. Cl. ......................................................... 623/2.36
(58) Field of Search .............................. 623/2.11, 2.36, 623/2.37; 606/232

(56) References Cited

U.S. PATENT DOCUMENTS

| | | | |
|---|---|---|---|
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,514,161 A | 5/1996 | Limousin | |
| 5,554,177 A | 9/1996 | Kieval et al. | |
| 5,562,698 A | 10/1996 | Parker | |
| 5,584,867 A | 12/1996 | Limousin et al. | |
| 5,601,600 A | 2/1997 | Ton | |

(Continued)

FOREIGN PATENT DOCUMENTS

| | | |
|---|---|---|
| EP | 0893133 A1 | 1/1999 |
| EP | 1050274 A1 | 11/2000 |
| EP | 1095634 A2 | 5/2001 |
| GB | 0741604 | 12/1955 |
| WO | WO 98/056435 A1 | 12/1998 |

(Continued)

OTHER PUBLICATIONS

Papageorgiou, P., et al., "Coronary Sinus Pacing Prevents Indcution of Atrial Fibrillation," Circulation 96: 1893–1898, Sep. 16, 1997.

*Primary Examiner*—Corrine McDermott
*Assistant Examiner*—Suzette J-J. Gherbi
(74) *Attorney, Agent, or Firm*—Wilson Sonsini Goodrich & Rosati

(57) ABSTRACT

An assembly for effecting the condition of a mitral valve annulus includes a mitral valve therapy device, a coupling structure carried by the device, a catheter, a second coupling structure, and a locking member. To implant the device, the device is first releasably locked to a pushing member by the coupling structures and the locking member. When the device is positioned within the coronary sinus adjacent the mitral valve annulus and deployed, the coupling structures may be released from each other by the release of the locking member.

10 Claims, 5 Drawing Sheets

U.S. PATENT DOCUMENTS

| | | | |
|---|---|---|---|
| 5,650,327 A | 7/1997 | Copeland et al. | |
| 5,660,228 A | 8/1997 | Steege et al. | |
| 5,676,671 A | 10/1997 | Inoue | |
| 5,733,325 A | 3/1998 | Robinson et al. | |
| 5,824,071 A | 10/1998 | Nelson et al. | |
| 5,891,193 A | 4/1999 | Robinson et al. | |
| 5,895,391 A | 4/1999 | Farnholtz | |
| 5,899,882 A | 5/1999 | Waksman et al. | |
| 5,908,404 A | 6/1999 | Elliott | |
| 5,928,258 A | 7/1999 | Khan et al. | |
| 5,935,161 A | 8/1999 | Robinson et al. | |
| 5,961,545 A | 10/1999 | Lentz et al. | |
| 5,988,494 A | 11/1999 | Fontaine | |
| 6,027,517 A | 2/2000 | Crocker et al. | |
| 6,077,295 A | 6/2000 | Limon et al. | |
| 6,077,297 A | 6/2000 | Robinson et al. | |
| 6,090,549 A | 7/2000 | Mirzabekov et al. | |
| 6,096,064 A | 8/2000 | Routh | |
| 6,099,552 A | 8/2000 | Adams | |
| 6,129,755 A | 10/2000 | Mathis et al. | |
| 6,190,406 B1 | 2/2001 | Duerig et al. | |
| 6,210,432 B1 | 4/2001 | Solem et al. | |
| 6,275,730 B1 | 8/2001 | KenKnight et al. | |
| 6,342,067 B1 | 1/2002 | Mathis et al. | |
| 6,352,553 B1 | 3/2002 | van der Burg et al. | |
| 6,352,561 B1 | 3/2002 | Leopold et al. | |
| 6,358,195 B1 | 3/2002 | Green et al. | |
| 6,395,017 B1 | 5/2002 | Dwyer et al. | |
| 6,402,781 B1 | 6/2002 | Langberg et al. | |
| 6,419,696 B1 | 7/2002 | Ortiz et al. | |
| 6,442,427 B1 | 8/2002 | Boute et al. | |
| 6,537,314 B2 | 3/2003 | Langberg et al. | |
| 6,569,198 B1 | 5/2003 | Wilson et al. | |
| 6,589,208 B2 | 7/2003 | Ewers et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,716,158 B2 | 4/2004 | Raman et al. | |
| 6,718,985 B2 | 4/2004 | Hlavka et al. | |
| 6,723,038 B1 | 4/2004 | Schroeder et al. | |
| 6,764,510 B2 | 7/2004 | Vidlund et al. | |
| 6,790,231 B2 | 9/2004 | Liddicoat et al. | |
| 6,793,673 B2 * | 9/2004 | Kowalsky et al. | 623/2.36 |
| 6,797,001 B2 * | 9/2004 | Mathis et al. | 623/2.37 |
| 6,800,090 B2 | 10/2004 | Alferness et al. | |
| 6,810,682 B1 | 11/2004 | Schuchart et al. | |
| 2001/0018611 A1 | 8/2001 | Solem et al. | |
| 2001/0044568 A1 | 11/2001 | Langberg et al. | |
| 2001/0049558 A1 | 12/2001 | Liddicoat et al. | |
| 2002/0016628 A1 | 2/2002 | Langberg eta l. | |
| 2002/0035381 A1 | 3/2002 | Houser et al. | |
| 2002/0042621 A1 | 4/2002 | Liddicoat et al. | |
| 2002/0042651 A1 | 4/2002 | Liddicoat eta l. | |
| 2002/0049468 A1 | 4/2002 | Streeter et al. | |
| 2002/0055774 A1 | 5/2002 | Liddicoat | |
| 2002/0065554 A1 | 5/2002 | Streeter | |
| 2002/0087173 A1 | 7/2002 | Alferness et al. | |
| 2002/0095167 A1 | 7/2002 | Liddicoat et al. | |
| 2002/0103533 A1 | 8/2002 | Langberg et al. | |
| 2002/0138044 A1 | 9/2002 | Streeter et al. | |
| 2002/0151961 A1 | 10/2002 | Lashinski et al. | |
| 2002/0169502 A1 | 11/2002 | Mathis | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2003/0004572 A1 | 1/2003 | Gobie et al. | |
| 2003/0018358 A1 | 1/2003 | Saadat | |
| 2003/0069636 A1 | 4/2003 | Solem et al. | |
| 2003/0078465 A1 | 4/2003 | Pai et al. | |
| 2003/0078654 A1 | 4/2003 | Taylor et al. | |
| 2003/0083538 A1 | 5/2003 | Adams et al. | |
| 2003/0088305 A1 | 5/2003 | Van Schie et al. | |
| 2003/0105520 A1 * | 6/2003 | Alferness et al. | 623/2.36 |
| 2003/0130730 A1 | 7/2003 | Cohn et al. | |
| 2003/0130731 A1 | 7/2003 | Vidlund et al. | |
| 2003/0135287 A1 | 7/2003 | Solem et al. | |
| 2003/0144697 A1 | 7/2003 | Mathis et al. | |
| 2003/0171776 A1 | 9/2003 | Adams et al. | |
| 2003/0171806 A1 * | 9/2003 | Mathis et al. | 623/2.36 |
| 2003/0212453 A1 | 11/2003 | Mathis et al. | |
| 2003/0225454 A1 * | 12/2003 | Mathis et al. | 623/2.36 |
| 2004/0019377 A1 | 1/2004 | Taylor et al. | |
| 2004/0039443 A1 | 2/2004 | Solem et al. | |
| 2004/0073302 A1 | 4/2004 | Rourke et al. | |
| 2004/0098116 A1 | 5/2004 | Calias et al. | |
| 2004/0102839 A1 | 5/2004 | Cohn et al. | |
| 2004/0102840 A1 * | 5/2004 | Solem et al. | 623/2.11 |
| 2004/0102841 A1 * | 5/2004 | Langberg et al. | 623/2.36 |
| 2004/0111095 A1 | 6/2004 | Gordon et al. | |
| 2004/0127982 A1 | 7/2004 | Machold et al. | |
| 2004/0133220 A1 | 7/2004 | Lashinski et al. | |
| 2004/0133240 A1 | 7/2004 | Adams et al. | |
| 2004/0133273 A1 * | 7/2004 | Cox | 623/2.11 |
| 2004/0138744 A1 | 7/2004 | Lashinski et al. | |
| 2004/0148019 A1 | 7/2004 | Vidlund et al. | |
| 2004/0148020 A1 | 7/2004 | Vidlund et al. | |
| 2004/0148021 A1 | 7/2004 | Cariedge et al. | |
| 2004/0153146 A1 * | 8/2004 | Lashinski et al. | 623/2.36 |
| 2004/0153147 A1 | 8/2004 | Mathis | |
| 2004/0158321 A1 | 8/2004 | Rueter et al. | |
| 2004/0176840 A1 | 9/2004 | Langberg | |
| 2004/0193191 A1 | 9/2004 | Starksen et al. | |
| 2004/0220654 A1 | 11/2004 | Mathis | |
| 2004/0220857 A1 | 11/2004 | Lapstun et al. | |
| 2004/0243227 A1 | 12/2004 | Starksen et al. | |
| 2004/0243228 A1 | 12/2004 | Kowalsky et al. | |

FOREIGN PATENT DOCUMENTS

| | | |
|---|---|---|
| WO | WO 00/044313 A1 | 8/2000 |
| WO | WO 00/060995 A3 | 10/2000 |
| WO | WO 01/000111 A1 | 1/2001 |
| WO | WO01/30248 | 5/2001 |
| WO | WO 01/050985 A1 | 7/2001 |
| WO | WO 01/054618 A1 | 8/2001 |
| WO | WO 01/087180 A2 | 11/2001 |
| WO | WO 02/00588 A1 | 1/2002 |
| WO | WO 02/000099 A2 | 1/2002 |
| WO | WO 02/001999 A2 | 1/2002 |
| WO | WO 02/0058881 | 1/2002 |
| WO | WO 02/034118 A2 | 5/2002 |
| WO | WO 02/047539 A2 | 6/2002 |
| WO | WO 02/053206 A2 | 7/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO 03/015611 A2 | 2/2003 |
| WO | WO 03/049647 A1 | 6/2003 |
| WO | WO 03/059198 A2 | 7/2003 |
| WO | WO 03/063735 A2 | 8/2003 |
| WO | WO 04/045463 A2 | 6/2004 |
| WO | WO2004/084746 | 10/2004 |

* cited by examiner

SYSTEM AND METHOD TO EFFECT THE MITRAL VALVE ANNULUS OF A HEART

CROSS-REFERENCE

This application is a divisional application of Ser. No. 10/331,143, now U.S. Pat. No. 6,793,673 filed Dec. 26, 2002, which is incorporated herein by reference in its entirety, and to which application we claim priority under 35 U.S.C. §121.

FIELD OF THE INVENTION

The present invention generally relates to a system and method to effect the mitral valve annulus of a heart. The present invention more particularly relates to a mitral valve annulus device, system, and method wherein the device is deployed and anchored in the coronary sinus of a heart adjacent the mitral valve annulus to reshape the mitral valve annulus.

BACKGROUND OF THE INVENTION

The human heart generally includes four valves. Of these valves, a most critical one is known as the mitral valve. The mitral valve is located in the left atrial ventricular opening between the left atrium and left ventricle. The mitral valve is intended to prevent regurgitation of blood from the left ventricle into the left atrium when the left ventricle contracts. In preventing blood regurgitation the mitral valve must be able to withstand considerable back pressure as the left ventricle contracts.

The valve cusps of the mitral valve are anchored to muscular wall of the heart by delicate but strong fibrous cords in order to support the cusps during left ventricular contraction. In a healthy mitral valve, the geometry of the mitral valve ensures that the cusps overlie each other to preclude regurgitation of the blood during left ventricular contraction.

The normal functioning of the mitral valve in preventing regurgitation can be impaired by dilated cardiomyopathy caused by disease or certain natural defects. For example, certain diseases may cause dilation of the mitral valve annulus. This can result in deformation of the mitral valve geometry to cause ineffective closure of the mitral valve during left ventricular contraction. Such ineffective closure results in leakage through the mitral valve and regurgitation. Diseases such as bacterial inflammations of the heart or heart failure can cause the aforementioned distortion or dilation of the mitral valve annulus. Needless to say, mitral valve regurgitation must not go uncorrected.

One method of repairing a mitral valve having impaired function is to completely replace the valve. This method has been found to be particularly suitable for replacing a mitral valve when one of the cusps has been severely damaged or deformed. While the replacement of the entire valve eliminates the immediate problem associated with a dilated mitral valve annulus, presently available prosthetic heart valves do not possess the same durability as natural heart valves.

Various other surgical procedures have been developed to correct the deformation of the mitral valve annulus and thus retain the intact natural heart valve function. These surgical techniques involve repairing the shape of the dilated or deformed valve annulus. Such techniques, generally known as annuloplasty, require surgically restricting the valve annulus to minimize dilation. Here, a prosthesis is typically sutured about the base of the valve leaflets to reshape the valve annulus and restrict the movement of the valve annulus during the opening and closing of the mitral valve.

Many different types of prostheses have been developed for use in such surgery. In general, prostheses are annular or partially annular shaped members which fit about the base of the valve annulus. The annular or partially annular shaped members may be formed from a rigid material, such as a metal, or from a flexible material.

While the prior art methods mentioned above have been able to achieve some success in treating mitral regurgitation, they have not been without problems and potential adverse consequences. For example, these procedures require open heart surgery. Such procedures are expensive, are extremely invasive requiring considerable recovery time, and pose the concomitant mortality risks associated with such procedures. Moreover, such open heart procedures are particularly stressful on patients with a compromised cardiac condition. Given these factors, such procedures are often reserved as a last resort and hence are employed late in the mitral regurgitation progression. Further, the effectiveness of such procedures is difficult to assess during the procedure and may not be known until a much later time. Hence, the ability to make adjustments to or changes in the prostheses to obtain optimum effectiveness is extremely limited. Later corrections, if made at all, require still another open heart surgery.

An improved therapy to treat mitral regurgitation without resorting to open heart surgery has recently been proposed. This is rendered possible by the realization that the coronary sinus of a heart is near to and at least partially encircles the mitral valve annulus and then extends into a venous system including the great cardiac vein. As used herein, the term "coronary sinus" is meant to refer to not only the coronary sinus itself but in addition, the venous system associated with the coronary sinus including the great cardiac vein. The therapy contemplates the use of a device introduced into the coronary sinus to reshape and advantageously effect the geometry of the mitral valve annulus.

The device includes an elongated flexible member having a cross sectional dimension for being received within the coronary sinus of the heart. The device includes an anchor at each of its ends. When placed in the coronary sinus, anchored and drawn taught, the device exerts an inward pressure on the mitral valve. The inward pressure increases the radius of curvature of the mitral valve annulus, or at least a portion of it, to promote effective valve sealing action and eliminate mitral regurgitation.

The device may be implanted in the coronary sinus using only percutaneous techniques similar to the techniques used to implant cardiac leads such as pacemaker leads. One prior proposed system for implanting the device includes an elongated introducer configured for being releasably coupled to the device. The introducer is preferably flexible to permit it to advance the device into the heart and into the coronary sinus through the coronary sinus ostium. To promote guidance, an elongated sheath is first advanced into the coronary sinus. Then, the device and introducer are moved through a lumen of the sheath until the device is in position within the coronary sinus. Because the device is formed of flexible material, it conforms to the curvatures of the lumen as it is advanced through the sheath. The sheath is then partially retracted. The distal end of the device is then anchored. Then, the sheath is retracted proximally past the proximal end of the device. The introducer is then drawn proximally to place the device in tension, where upon the proximal anchor is set. The procedure is then completed by the release of the introducer from the device and retraction of the introducer and sheath. As a result, the device is left within the coronary sinus to exert the inward pressure on the mitral valve annulus.

While the foregoing represents great adjunctment in the art, further improvement is possible. For example, in the prior delivery system, described hereinbefore, release of the introducer from the device is difficult. The device and introducer carried interlocking couplers which required an uncoupling action to be applied to the introducer to unlock the device from the introducer. This action could cause the device position to change and adversarily alter its effectiveness. Still further, neither the device nor the introducer were well suited for recapturing the device for removal. Recapture and removal of the device may be advisable if exchange to a device of different dimension is considered to be more appropriate for a given patient.

Hence, there is a need for a more effective device, delivery assembly, and method to deliver a mitral valve annulus therapy device into the coronary sinus adjacent the mitral valve annulus and to release the device in a manner which leaves the device positioning unaffected. Still further, there is a need for such a device and assembly which provides recapture of the device should such recapture be required for removal of the device. The present invention addresses these needs.

SUMMARY OF THE INVENTION

The invention provides an assembly for effecting the condition of a mitral valve annulus of a heart. The assembly includes a mitral valve therapy device that reshapes the mitral valve annulus of the heart when placed within the coronary sinus of the heart adjacent the mitral valve annulus. The mitral valve therapy device has a proximal end including a coupling structure. The assembly further includes a catheter having a lumen that directs the mitral valve therapy device into the coronary sinus of the heart, a second coupling structure that is lockable on the device coupling structure, and a locking member that locks the device coupling structure to the second coupling structure and that releases the device coupling structure from the second coupling structure.

The assembly may further include a pusher member that pushes the device through the catheter lumen. The pusher member has a distal end that engages the device proximal end. The pusher member may carry the second coupling structure at the distal end of the pusher member.

The device coupling structure may comprise a hoop structure. The second coupling structure may also comprise a hoop structure. The locking member comprises a pin that extends through the hoop structures to lock the coupling structures together and that is retractable to release the hoop structures. The catheter has a distal end and the pin is preferably long enough to extend through the distal end of the catheter. The pusher member may be an elongated coil.

The device coupling structure and the second coupling structure may alternatively comprise a pair of interlocking structures and the locking member may comprise a slide-lock sheath closely fitted to the interlocking structures. The interlocking structures and the slide-lock sheath may be tubular. The pusher member has a distal end that engages the device proximal end, and carries the second coupling structure. The locking member may further include a tether that extends from the slide-lock sheath to and through the catheter lumen to permit the tether to pull proximally on the slide-lock sheath for releasing the interlocking structures.

The assembly may further include a retractor configured to extend through the catheter lumen and grip the device coupler. This permits retraction of the device through the catheter.

The invention further provides an assembly for effecting the condition of a mitral valve annulus of a heart comprising device means for reshaping the mitral valve annulus of the heart when placed within the coronary sinus of the heart adjacent the mitral valve annulus. The device means has a proximal end including a coupling means for coupling the device means. The assembly further comprises catheter means having a lumen that directs the mitral valve therapy device into the coronary sinus of the heart, second coupling means for locking with the device coupling means, and locking means for locking the device coupling means to the second coupling means and releasing the device coupling means from the second coupling means.

The present invention further provides a method of implanting a mitral valve therapy device to effect the condition of a mitral valve annulus of a heart. The method includes the steps of feeding a catheter having a lumen into the coronary sinus of the heart, locking the device to a deployment member with a locking member, and directing the mitral valve therapy device through the catheter lumen into the coronary sinus with the deployment member. The method further includes the steps of positioning the mitral valve therapy device in the coronary sinus with the deployment member, releasing the locking member from the device and the deployment member coupler, removing the deployment member and the locking member from the catheter lumen, and removing the catheter from the coronary sinus.

The invention still further provides a method of effecting the condition of a mitral valve annulus of a heart. The method includes the steps of feeding a catheter having a lumen into the coronary sinus of the heart, aligning a mitral valve therapy device coupler of a mitral valve therapy device to a deployment member coupler, and locking the device coupler to the deployment member coupler with a locking member. The method further includes directing the mitral valve therapy device through the catheter lumen into the coronary sinus with the deployment member, positioning the mitral valve therapy device in the coronary sinus with the deployment member, releasing the locking member from the device coupler and the deployment member coupler, removing the deployment member, the deployment member coupler and the locking member from the catheter lumen, and removing the catheter from the coronary sinus.

The invention further provides an assembly for effecting the condition of a mitral valve annulus of a heart which includes a mitral valve therapy device that reshapes the mitral valve annulus of the heart when placed within the coronary sinus of the heart adjacent the mitral valve annulus, the mitral valve therapy device having a proximal end including a coupling structure and a guide member that directs the mitral valve therapy device into the coronary sinus of the heart. The assembly further includes a second coupling structure that is lockable on the device coupling structure, and a locking member that locks the device coupling structure to the second coupling structure and that releases the device coupling structure from the second coupling structure.

The invention further provides an assembly for effecting the condition of a mitral valve annulus of a heart. The assembly includes device means for reshaping the mitral valve annulus of the heart when placed within the coronary sinus of the heart adjacent the mitral valve annulus, the device means having a proximal end including a coupling means for coupling the device means, guide means for directing the mitral valve therapy device into the coronary sinus of the heart, second coupling means for locking with the device coupling means, and locking means for locking the device coupling means to the second coupling means and releasing the device coupling means from the second coupling means.

The invention still further provides a method of implanting a mitral valve therapy device to effect the condition of a mitral valve annulus of a heart. The method includes the steps of feeding a guide member into the coronary sinus of the heart, locking the device to a deployment member with a locking member, directing the mitral valve therapy device along the guide member into the coronary sinus with the deployment member, positioning the mitral valve therapy device in the coronary sinus with the deployment member, releasing the locking member from the device and the deployment member coupler, and removing the deployment member, the locking member, and the guide member from the coronary sinus.

BRIEF DESCRIPTION OF THE DRAWINGS

The features of the present invention which are believed to be novel are set forth with particularity in the appended claims. The invention, together with further aspects and advantages thereof, may best be understood by making reference to the following description taken in conjunction with the accompanying drawings, in the several figures of which like reference numerals identify identical elements, and wherein:

DETAILED DESCRIPTION OF THE INVENTION

Figure 1:
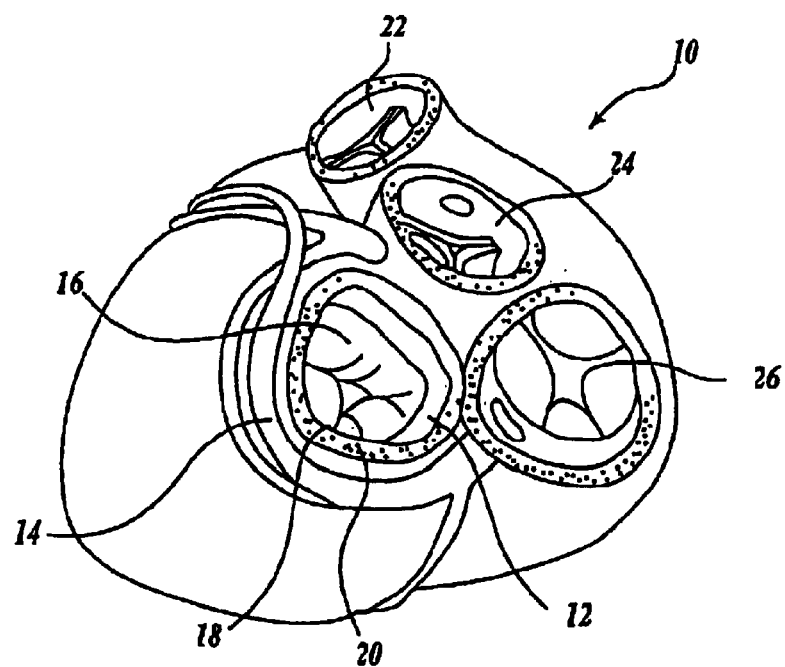
FIG. 1 is a superior view of a human heart with the atria removed.

Referring now to FIG. 1, it is a superior view of a human heart 10 with the atria removed to expose the mitral valve 12, and the coronary sinus 14 of the heart 10. Also generally shown in FIG. 1 are the pulmonary valve 22, the aortic valve 24, and the tricuspid valve 26 of the heart 10.

The mitral valve 12 includes an anterior cusp 16, a posterior cusp 18 and an annulus 20. The annulus encircles the cusps 16 and 18 and maintains their spacing to provide a complete closure during a left ventricular contraction. As is well known, the coronary sinus 14 partially encircles the mitral valve 12 adjacent to the mitral valve annulus 20. As is also known, the coronary sinus is part of the venus system of the heart and extends along the AV groove between the left atrium and the left ventricle. This places the coronary sinus essentially within the same plane as the mitral valve annulus making the coronary sinus available for placement of the mitral valve therapy device of the present invention therein.

Figure 2:
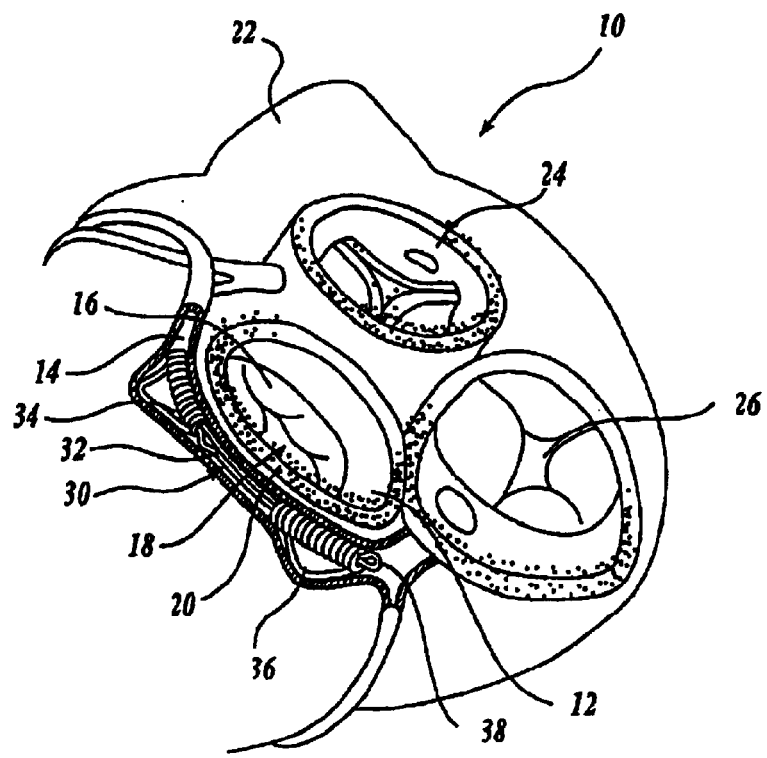
FIG. 2 is a superior view of a human heart similar to FIG. 1 illustrating a mitral valve therapy device embodying the present invention deployed therein and which may be by deployed an assembly embodying the present invention.

FIG. 2 shows a mitral valve therapy device 30 embodying the present invention shown deployed in the coronary sinus 14 of the heart 10 adjacent the mitral valve annulus 20 for effecting the geometry of the mitral valve annulus. The device 30 takes the form of an elongated body 32 which includes a distal anchor 34 and a proximal anchor 36.

The anchors 34 and 36 are shown in FIG. 2 in their deployed configuration. A more complete description of the anchors 34 and 36 may be had in copending application Ser. No. 10/142,637, filed May 8, 2002 for BODY LUMEN DEVICE ANCHOR, DEVICE AND ASSEMBLY which is assigned to the assignee of the present invention and hereby incorporated herein by reference. In deploying the device 30 in the coronary sinus, the distal anchor 34 is first deployed to anchor the distal end of the device 30. In the anchoring process, the anchor 34 is expanded outwardly to anchor the device in the coronary sinus against both bidirectional longitudinal and rotational movement. This allows the device 30 to be tightened within the coronary sinus by pulling of the device's proximal end. Then, the proximal anchor 36 is deployed. The device 30, which may be formed from Nitinol or stainless steel, for example, now exerts an inward pressure on the mitral valve annulus 20 to advantageously effect its geometry.

Figure 3:
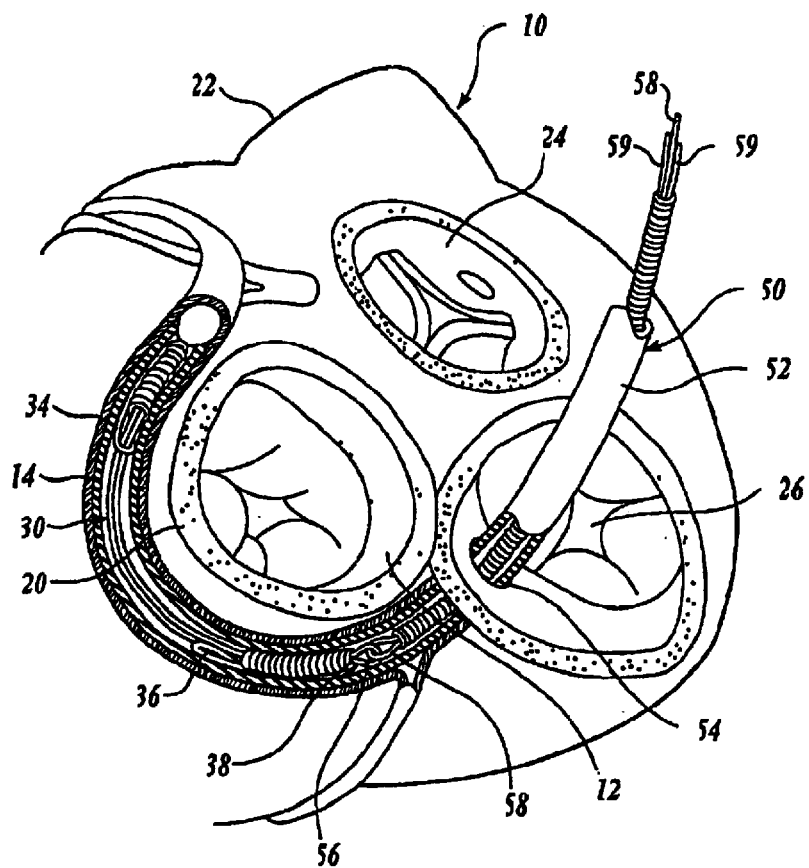
FIG. 3 is a superior view similar to FIG. 1 with portions cut away illustrating the device of FIG. 2 being deployed by a deployment assembly embodying the present invention.

The device 30 along with its deployment system 50 is illustrated in FIG. 3. As shown, the device is in the process of being implanted in the coronary sinus 14 of the heart 10. Its proximal anchor 36 and distal anchor 34 have yet been deployed. The deployment system 50 includes an elongated catheter 52, an elongated pusher 54, a coupling structural member 56 and a locking pin 58. As may be noted in FIG. 4, the proximal end of the device 30 includes a coupling loop 38. The pusher 54 is preferably an elongated coil having a center lumen 55. The coupling member 56 is formed from a cable that is provided with a loop 57. The legs or ends 59 of the loop 57 extend proximally through the lumen 55 and out the proximal end of the pusher 54.

Figure 4:
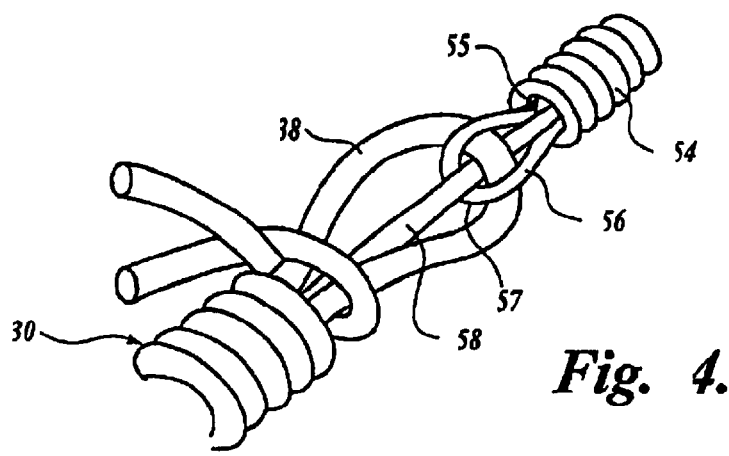
FIG. 4 is a partial perspective view to an enlarged scale illustrating the coupling members and locking member of a first embodiment of the present invention.

The locking pin 58 also extends proximally out of the proximal end of the pusher 54. As shown in FIG. 4, the coupling loops 38 and 57 are aligned to overlap and the locking pin 58 is extended through the overlapping loops. This causes the device 30 to be releasably locked to the pusher 54.

Figure 5:
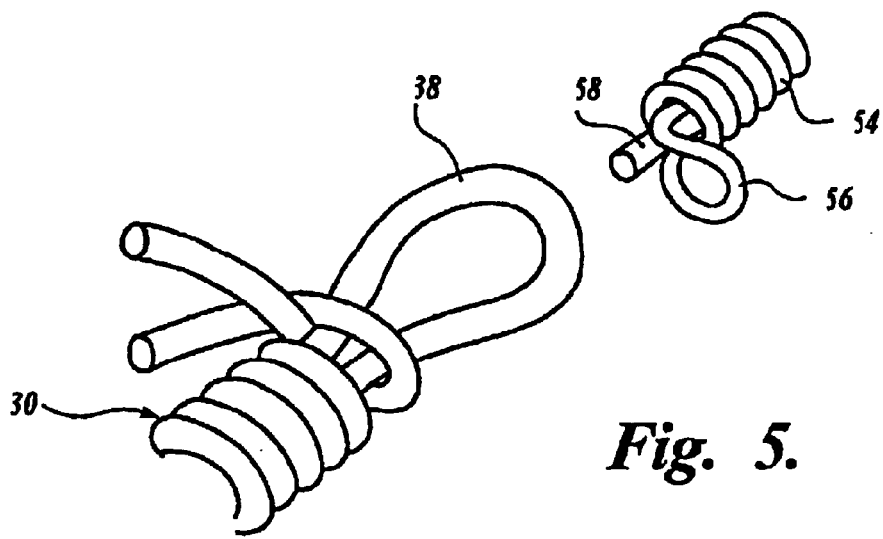
FIG. 5 is a view similar to FIG. 4 illustrating the release of the coupling structures.

In deploying the device 30, the catheter 52 is first fed into the coronary sinus 14 adjacent the mitral valve annulus 20. The device 30 and pusher 54 are then releasably locked together as shown in FIG. 4. The device is then loaded into the catheter 52. The pusher 54 follows the device into the catheter 52 and is then advanced along the catheter to push the device 30 distally down the catheter to a predetermined position adjacent the mitral valve annulus 14 at the distal end of the catheter 52. Thereafter, the device is maintained in a stationary position by the pusher 54 as the catheter 52 is partially withdrawn to expose the distal anchor 34. Once the distal anchor 34 is exposed, it is deployed in a manner as fully described in the aforementioned copending application Ser. No. 10/142,637. Once the distal anchor 34 is deployed, the catheter 50 is then retracted proximally of the proximal anchor 36. This exposes the proximal anchor 36. Once the proximal anchor is exposed, the pusher 54 is pulled proximally for tightening the device within the coronary sinus and to an extent which results in the desired effect on the geometry of the mitral valve annulus 20. During this adjustment process, mitral regurgitation may be monitored and the device adjusted for optimal results. When the device 30 is in its final position within the coronary sinus 14, the proximal anchor 36 may then be deployed. The beneficial effect of the device may now again be evaluated. Once the device is ready for chronic implant, the locking pin 58 may be pulled proximally from the proximal end of the pusher 54 as shown in FIG. 5 to disengage the coupling members 38 and 56. With the pusher 54 now free from the device 30, the pusher 54, catheter 52, coupling member 56 and locking pin 58 may then be removed from the heart.

As can be appreciated by those skilled in the art, guide members, other than a guide catheter as shown herein, may be used to direct the device into the coronary sinus. For example, a guide wire, of the type well known in the art may alternatively be employed to guide the device there along into the coronary sinus without departing from-the present invention.

Figure 6:
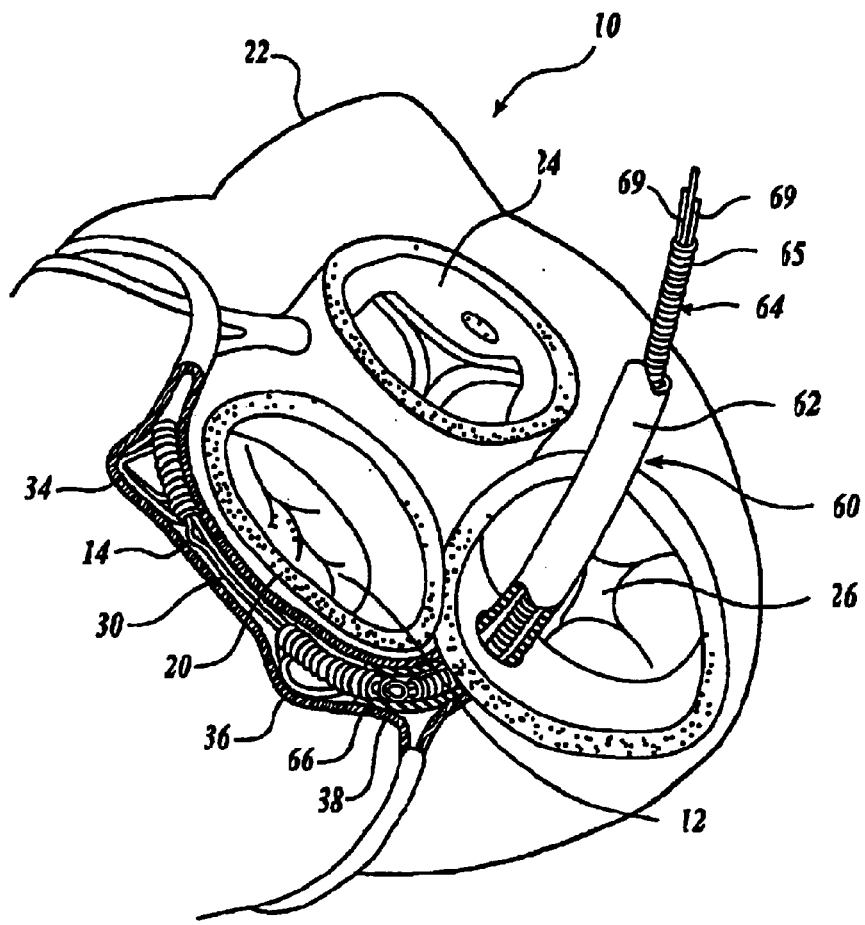
FIG. 6 is a superior view similar to FIG. 1 illustrating recapture of the deployed device.
Figure 7:
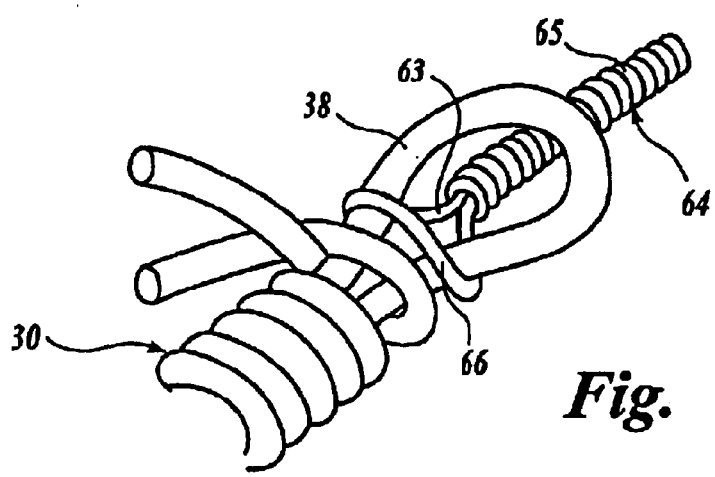
FIG. 7 is a partial perspective view to an enlarged scale illustrating the recapture of the device.

FIGS. 6 and 7 illustrate the manner in which the device 30 may be removed from the coronary sinus 14 if necessary in accordance with further aspects of the present invention. As may be seen in FIGS. 6 and 7, the device 30 may be removed from the coronary sinus 14 with a retractor assembly 60. The retractor assembly includes the catheter 62, and a retractor 64 comprising an elongated coil 65 and a coupling member 66. The elongated coil 65 of the retractor 64 is essentially identical to the pusher 54 as illustrated in FIGS. 3–5. The coupling member 66 may be a cable which extends down the center lumen of the elongated coil 65 to form a loop structure 66 and which then returns through the center lumen of the elongated coil 65 such that the free ends 69 of the cable 63 extend out the proximal end of the elongated coil 65. As also seen in FIGS. 6 and 7, if the device 30 is to be removed from the coronary sinus 14, the cable 63 is threaded into the elongated coil 65 to form the loop structure 66. With the retractor 64 thus formed, the retractor is then guided down the catheter 62 to the proximal end of the device 30 and more specifically to the coupling loop member 38 of the device 30. The loop 66 of the cable 63 is then wrapped about the loop coupling member 38 of the device 30 and the free ends 69 of the cable are drawn proximally to tighten the loop structure 66 about the loop coupling member 38. The retractor 64 now has a grip on the device 30. With the device 30 now being firmly held by the retractor 64, the retractor 64 may be pulled proximally within the catheter 62 to impart proximal movement to the device 30. When the anchors 34 and 36 of the device 30 engage the distal end of the catheter 62, they will be collapsed to disengage from the coronary sinus. The device may now be removed by pulling on the retractor 64 proximally within the catheter 62 until the device is fully removed from the heart and the patient. Alternatively, the device may be drawn into the catheter. The catheter and the device may then be withdrawn together from the patient.

Figure 8:
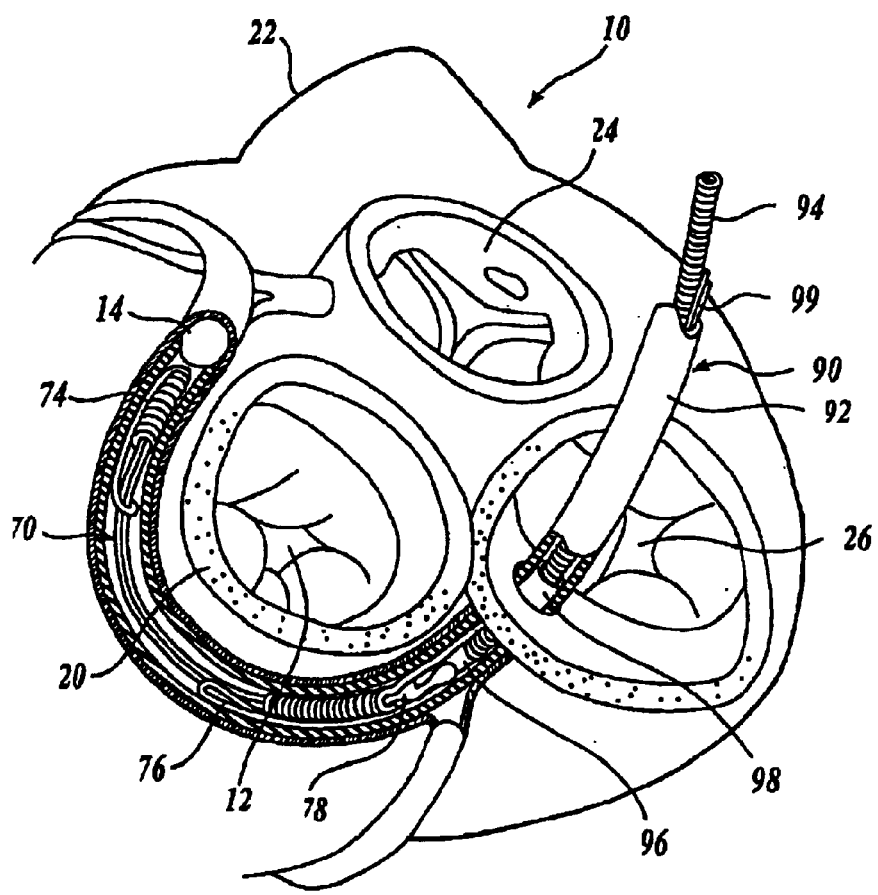
FIG. 8 is a superior view similar to FIG. 1 illustrating a further embodiment of the present invention.
Figure 9:
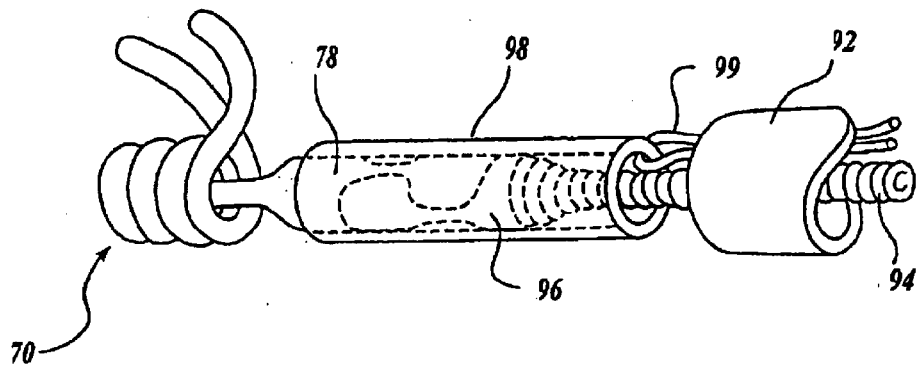
FIG. 9 is a partial perspective view of the coupling and locking arrangement of FIG. 8.
Figure 10:
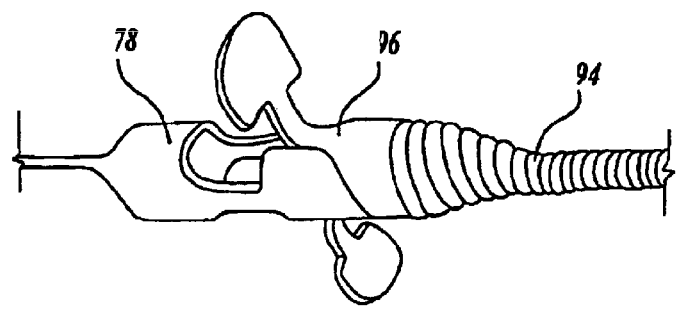
FIG. 10 is a partial perspective view illustrating the release of the coupling members of FIG. 8.

FIGS. 8–10 illustrate a further embodiment of the present invention for releasably locking a pusher member to a mitral valve therapy device for implanting the mitral valve therapy device adjacent the mitral valve annulus within the coronary sinus of the heart.

As illustrated in FIG. 8, the mitral valve therapy device 70 is elongated and includes a distal anchor 74 and a proximal anchor 76. The anchors are not yet deployed. The device 70 further includes, at its proximal end, a coupling structure 78.

For deploying the device 70, a deployment system 90 is also illustrated. The deployment system includes a catheter 92, a pusher member 94, a coupling structure 96 at the distal end of the pusher 94, and a locking member 98. As will be best seen in FIG. 9, the coupling member 78 of the device 70 and the coupling member 96 of the pusher 94 form a pair of interlocking structures. The coupling structures 78 and 96 are tubular and the locking member 98 is also tubular.

When it is desired to implant the device 70, the device 70 is coupled to the pusher 98 by the interlocking structures of the coupling members 78 and 96 which are held together and in place by the locking member 98. Then, as previously described in the previous embodiment, the device and pusher member are fed down the catheter 92 until the device reaches a desired position within the coronary sinus adjacent the mitral valve annulus 20. Once in this position, the device is held stationary by the pusher member 94 while the catheter 92 is retracted to expose the distal anchor 74. The distal anchor 74 may now be deployed in a manner as described in the aforementioned copending application Ser. No. 10/142,637. With the distal anchor 74 deployed, the catheter 92 is then retracted until it is proximal to the proximal anchor 76. The pusher 94 may then be pulled to tighten the device within the coronary sinus. Once the device 70 has been tightened to a desired degree, as confirmed by device effectiveness evaluation, the device 70 is ready for chronic implant.

When the device 70 is to be left within the coronary sinus 14, the tether 99 is pulled to slide the locking member 98 off of the interlocking structures 78 and 96. The coupling structures of the pusher 94 may be prestressed for disengaging the coupling structure 78 of the device 70 when the locking member 98 is pulled proximal to the interlocking structures. The device 70 is now free from the pusher member 94. The pusher member 94 together with the tether, locking member, and catheter 92 may be removed from the heart. With the implant of the device 70 completed, the device 70 is left within the coronary sinus adjacent the mitral valve annulus 20 to treat the mitral valve such as by eliminating mitral regurgitation.

As illustrated in FIG. 10, the coupling structure 96 is prestressed to deflect outwardly when the tubular locking member 98 is pulled proximally to disengage the device 70 from the pusher 94. Alternatively, the coupling structure 96 may be prestressed inwardly with a locking pin (not shown) extending into coupling stricture 78 to maintain the locked arrangement. Here, proximal pulling of the pin would cause the coupling structure 96 to deflect inwardly to disengage the coupling structure 78 and 96.

While particular embodiments of the present invention have been shown and described, modifications may be made, and it is therefore intended in the appended claims to cover all such changes and modifications which fall within the true spirit and scope of the invention.

What is claimed:

1. An assembly for effecting the mitral valve annulus of a heart comprising:

a mitral valve therapy device that reshapes the mitral valve annulus of the heart when placed within the coronary sinus of the heart adjacent the mitral valve annulus, the mitral valve therapy device having a proximal end including a coupling structure;

a catheter having a lumen that directs the mitral valve therapy device into the coronary sinus of the heart;

a second coupling structure that is lockable on the device coupling structure, the device coupling structure and the second coupling structure comprising a pair of interlocking structures;

a locking member that locks the device coupling structure to the second coupling structure and that releases the device coupling structure from the second coupling structure, the locking member comprising a slide-lock sheath closely fitted to the interlocking structures; and a pusher member that pushes the device through the catheter lumen, the pusher member having a distal end that engages the device proximal end, and wherein the pusher member carries the second coupling structure at the distal end of the pusher member.

2. The assembly of claim 1 wherein the locking member further comprises a tether that extends from the slide-lock sheath to and through the catheter lumen to permit the tether to pull proximally on the slide-lock sheath for releasing the interlocking structures.

3. An assembly for effecting the mitral valve annulus of a heart comprising:

a mitral valve therapy device that reshapes the mitral valve annulus of the heart when placed within the coronary sinus of the heart adjacent the mitral valve annulus, the mitral valve therapy device having a proximal end including a coupling structure;

a catheter having a lumen that directs the mitral valve therapy device into the coronary sinus of the heart;

a second coupling structure that is lockable on the device coupling structure;

a locking member that locks the device coupling structure to the second coupling structure and that releases the device coupling structure from the second coupling structure; and a retractor configured to extend through the catheter lumen and grip the device coupler to permit retraction of the device through the catheter.

4. The assembly of claim 3 further comprising a pusher member configured to extend through the catheter lumen and that pushes the device through the catheter lumen, the pusher member having a lumen and a distal end adapted to engage the device proximal end, and wherein the retractor is configured to extend down the pusher lumen to engage the device coupler.

5. An assembly for effecting the condition of a mitral valve annulus of a heart comprising:

device means for reshaping the mitral valve annulus of the heart when placed within the coronary sinus of the heart adjacent the mitral valve annulus, the device means having a proximal end including a coupling means for coupling the device means;

catheter means having a lumen that directs the mitral valve therapy device into the coronary sinus of the heart;

second coupling means for locking with the device coupling means;

locking means for locking the device coupling means to the second coupling means and releasing the device coupling means from the second coupling means; and retracting means for engaging the device coupling means and removing the device means from the coronary sinus.

6. A method of effecting the condition of a mitral valve annulus of a heart, the method comprising the steps of:

feeding a catheter having a lumen into the coronary sinus of the heart;

aligning a mitral valve therapy device coupler of a mitral valve therapy device to a deployment member coupler;

locking the device coupler to the deployment member coupler with a locking member;

directing the mitral valve therapy device through the catheter lumen into the coronary sinus with the deployment member;

positioning the mitral valve therapy device in the coronary sinus with the deployment member;

releasing the locking member from the device coupler and the deployment member coupler;

removing the deployment member, the deployment member coupler and the locking member from the catheter lumen; and removing the catheter from the coronary sinus.

7. The method of claim 6 comprising the additional steps of:

evaluating a condition of the mitral valve following the first recited removing step;

based upon results of the evaluation, feeding a device retractor through the catheter lumen;

capturing the device coupler with the retractor; and removing the device from the coronary sinus through the catheter with the retractor.

8. A method of implanting a mitral valve therapy device to effect the condition of a mitral valve annulus of a heart, the method comprising the steps of:

feeding a catheter having a lumen into the coronary sinus of the heart;

locking the device to a deployment member with a locking member;

directing the mitral valve therapy device through the catheter lumen into the coronary sinus with the deployment member;

positioning the mitral valve therapy device in the coronary sinus with the deployment member;

releasing the locking member from the device and the deployment member coupler;

removing the deployment member and the locking member from the catheter lumen; and removing the catheter from the coronary sinus.

9. The method of claim 8 comprising the additional steps of:

evaluating a condition of the mitral valve following the first recited removing step;

based upon results of the evaluation, feeding a device retractor through the catheter lumen;

capturing the device with the retractor; and removing the device from the coronary sinus through the catheter with the retractor.

10. A method of implanting a mitral valve therapy device to effect the condition of a mitral valve annulus of a heart, the method comprising the steps of:

feeding a guide member into the coronary sinus of the heart;

locking the device to a deployment member with a locking member;

directing the mitral valve therapy device along the guide member into the coronary sinus with the deployment member;

positioning the mitral valve therapy device in the coronary sinus with the deployment member;

releasing the locking member from the device and the deployment member coupler; and removing the deployment member, the locking member, and the guide member from the coronary sinus.

* * * * *